United States Patent [19]

Partenheimer et al.

[11] Patent Number: 5,041,633

[45] Date of Patent: Aug. 20, 1991

[54] PROCESS FOR THE PRODUCTION OF AN AROMATIC POLYCARBOXYLIC ACID

[75] Inventors: Walter Partenheimer, Naperville; Gregory P. Hussmann, Warrenville; Juergen K. Holzhauer, Naperville; Stephen V. Hoover, Aurora, all of Ill.

[73] Assignee: Amoco Corporation, Chicago, Ill.

[21] Appl. No.: 43,838

[22] Filed: Apr. 28, 1987

Related U.S. Application Data

[63] Continuation-in-part of Ser. No. 790,538, Oct. 23, 1985, Pat. No. 4,719,311.

[51] Int. Cl.$^5$ .................. C07C 51/265; C07C 51/255
[52] U.S. Cl. ..................................... 562/413; 562/416
[58] Field of Search .................................. 562/413, 416

[56] References Cited

U.S. PATENT DOCUMENTS

| | | | |
|---|---|---|---|
| 4,197,412 | 4/1980 | Kimura et al. | 562/416 |
| 4,230,882 | 10/1980 | Seko et al. | 562/416 |
| 4,299,977 | 11/1981 | Kuhlman et al. | 562/416 |
| 4,719,311 | 1/1988 | Partenheimer | 562/413 |

Primary Examiner—Werren B. Lone
Attorney, Agent, or Firm—James R. Henes; William H. Magidson; Ralph C. Medhurst

[57] ABSTRACT

A method for producing an aromatic polycarboxylic acid by oxidizing an aromatic feed compound having at least 3 oxidizable ring substituents, wherein, after initiation of the oxidation water from an external source is added and the reaction temperature is raised.

20 Claims, 1 Drawing Sheet

ADDITION OF SELECTED AROMATIC ACIDS TO A Co/Mn/Br CATALYZED OXIDATION OF PSEUDOCUMENE AT A WATER LEVEL OF 0.3 %

ADDITION OF SELECTED AROMATIC ACIDS TO A Co/Mn/Br CATALYZED OXIDATION OF PSEUDOCUMENE AT A WATER LEVEL OF 0.3 %

PROCESS FOR THE PRODUCTION OF AN AROMATIC POLYCARBOXYLIC ACID

RELATED CASE

This application is a continuation-in-part of patent application Ser. No. 790,538, filed on Oct. 23, 1985, now U.S. Pat. No. 4,719,311.

BACKGROUND OF THE INVENTION

1. Field of the Invention

The field of this invention relates to the liquid-phase oxidation of an aromatic compound having oxidizable substituents to the corresponding aromatic polycarboxylic acid, and more particularly concerns the oxidation of an aromatic compound having at least three oxidizable substituents.

2. Description of the Prior Art

Heretofore, it has not been possible generally to achieve high yields of the resulting aromatic polycarboxylic acid when a aromatic compound having three or more oxidizable substituents are oxidized in the liquid phase and in a solvent to its corresponding aromatic polycarboxylic acid in the presence of a catalyst having cobalt, manganese and bromine components. This problem is particularly severe when an aromatic compound having four or more oxidizable substituents is being oxidized.

The reasons for this problem are not clear, but an aromatic polycarboxylic acid produced when three or more oxidizable substituents, especially on the same aromatic ring, are oxidized has a propensity to precipitate the metal component(s) of the aforesaid catalyst from the reaction mixture. The aforesaid catalyst is also deactivated when an aromatic polycarboxylic acid having two or more carboxylic groups ortho to each other on the aromatic ring is formed. For example, when durene is oxidized to pyromellitic acid, the deactivation of the aforesaid catalyst occurs when the oxidation of durene is about fifty percent complete. For an aromatic polycarboxylic acid having more than two carboxylic acid groups ortho to each other on the aromatic ring, deactivation of the aforesaid catalyst occurs when the oxidation reaction is less than fifty percent complete.

OBJECTS OF THE INVENTION

It is therefore a general object of the present invention to provide an improved method for the aforesaid oxidation which overcomes the problems of the prior art methods.

More particularly, it is an object of the present invention to provide an improved method for the aforesaid oxidation which affords a high yield of the resulting aromatic polycarboxylic acid.

A related object of the present invention is to provide an improved method for the aforesaid oxidation which affords a substantial reduction both in the precipitation of the metal components of the aforesaid catalyst and in the deactivation of the aforesaid catalyst.

Other objects and advantages of the invention will become apparent upon reading the following detailed description and appended claims, and upon reference to the accompanying drawing.

SUMMARY OF THE INVENTION

These objects are achieved by an improved method for producing an aromatic polycarboxylic acid product comprising: oxidizing an aromatic feed compound having at least one phenyl ring or a condensed aromatic ring system and having at least 3 oxidizable ring substituents, said oxidizable substituents comprising alkyl groups, carbonyl-containing alkyl groups, or hydroxy-substituted alkyl groups, with such alkyl groups containing 1-3 carbon atoms, with at least 2 oxidizable substituents on one phenyl ring or on one ring in the condensed aromatic ring system, with an oxygen-containing gas in the liquid phase at an elevated temperature and pressure, in a solvent comprising a $C_2$-$C_6$ monocarboxylic acid, and in the presence of an oxidation catalyst comprising cobalt, manganese, and bromine components, with a volume ratio of solvent-to-feed in the range from about 1:1 to about 10:1, wherein, the reaction temperature is in the range of from about 93° C. to about 199° C. during the first third of the stoichiometrically complete conversion of the aforesaid feed compound to the aforesaid product and is increased at least about 14° C. to the range of from about 176° C. to about 249° C. during the last two thirds of the aforesaid stoichiometrically complete conversion, and wherein water is added from an external source during the aforesaid last two thirds of the stoichiometrically complete conversion to a level in the range of from about 5 to about 75 weight percent of the total solvent of the monocarboxylic acid and water.

BRIEF DESCRIPTION OF THE DRAWING

For a more complete understanding of the present invention, reference should now be made to the embodiments illustrated in greater detail in the accompanying drawing and described below by way of examples of the invention. In the drawing.

Figure 1:
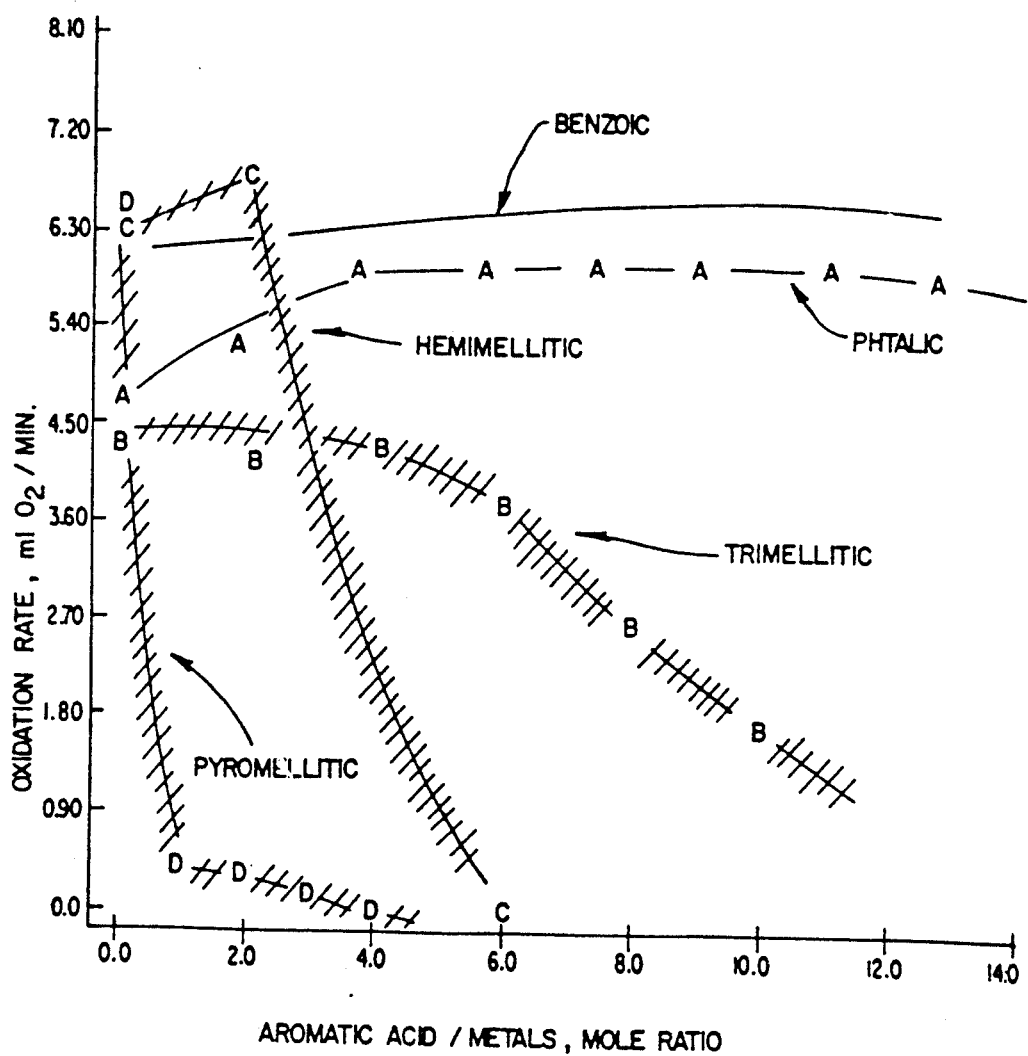
FIG. 1 is a plot of the rate of oxidation of pseudocumene versus the mole ratio of (a) trimellitic, hemimellitic, or (b) pyromellitic acid added to the reaction system-to-catalyst metals.

It should be understood that, in certain instances, details which are not necessary for an understanding of the present invention or which render other details difficult to perceive may have been omitted. It should be understood, of course, that the invention is not necessarily limited to the particular embodiments illustrated herein.

DETAILED DESCRIPTION OF THE PREFERRED EMBODIMENTS

Suitable feedstocks for use in the method of this invention are aromatic compounds having at least one phenyl group or a condensed aromatic ring system and having at least 3 oxidizable ring substituents, with at least 2 oxidizable substituents on one phenyl ring or on one ring in the condensed aromatic ring system. The oxidizable substituents comprise alkyl groups, carbonyl-containing alkyl groups, or hydroxy-substituted alkyl groups, with such alkyl groups containing 1-3 carbon atoms. Preferably at least 2 such oxidizable substituents are ortho to each other on one phenyl ring or on one ring in the condensed aromatic ring system of the aromatic feed compound. Typically, the aromatic portion of such a compound is a phenyl or naphthyl ring, and the oxidizable substituents thereon contain from 1 to 3 carbon atoms and are either alkyl groups such as methyl, ethyl or propyl, or carbonyl groups such as formyl, acetyl or propionyl, or are a combination of alkyl and carbonyl groups. Preferably, the feedstock is a trimethylbenzene such as 1,2,3- or 1,2,4-trimethylbenzene, a tetramethylbenzene such as 1,2,4,5-tetramethylbenzene (durene) or 1,2,3,4- or 1,2,3,5-tetramethylbenzene, hexamethylbenzene, a dimethylbenzaldehyde, a trimethylbenzaldehyde. More perferably, the feedstock is durene or 2,4,5-trimethylbenzaldehyde.

Suitable solvents for use in the method of this invention comprise any aliphatic $C_2$–$C_6$ monocarboxylic acid such as acetic acid, propionic acid, n-butyric acid, isobutyric acid, n-valeric acid, trimethylacetic acid, and caproic acid, and mixtures thereof with water, and, as described hereinbelow at least during the last half or two-thirds of the reaction, must contain such a mixture. Preferably, the solvent comprises acetic acid and water.

The weight ratio of monocarboxylic acid solvent-to-aforesaid aromatic feedstock compound is from about 0.5:1, preferably from about 1:1, more preferably from about 2:1, to about 15:1, preferably to about 10:1, and more preferably to about 8:1.

The source of molecular oxygen employed in the method of this invention can vary in molecular oxygen content from that of air to oxygen gas. Air is the preferred source of molecular oxygen. In order to avoid the formation of explosive mixtures, the oxygen-containing gas fed to the reactor should provide an exhaust gas-vapor mixture (vented from the oxidation reactor as described below) containing from 0.5 to 18 volume percent oxygen (measured on a solvent-free basis). For example, a feed rate of the oxygen-containing gas sufficient to provide oxygen in the amount of from 1.5 to 4.5 moles per carbon atom in the oxidizable substituents being oxidized will provide such 0.5 to 18 volume percent of oxygen (measured on a solvent-free basis) in the gas-vapor mixture withdrawn from the reactor.

The catalyst employed in the method of this invention comprises cobalt, manganese, and bromine components, and can additionally comprise accelerators known in the art. Preferably, the catalyst consists essentially of the cobalt-, manganese-, and bromine-containing components. Each of the cobalt and manganese components can be provided in any of its known ionic or combined forms that provide soluble forms of cobalt, manganese, and bromine in the solvent in the reactor. For example, when the solvent is an acetic acid medium, cobalt and/or manganese carbonate, acetate tetrahydrate, and/or bromine can be employed. The bromine-to-total cobalt and manganese milligram atom ratios described hereinbelow are provided by a suitable source of bromine. Such bromine sources include molecular bromine ($Br_2$), or ionic bromide (e.g., HBr, NaBr, KBr, $NH_4Br$, etc.), or organic bromides which are known to provide bromide ions at the operating temperature of the oxidation (e.g., bromobenzenes, benzyl-bromide, mono- and di-bromoacetic acid, bromoacetyl bromide, tetrabromoethane, ethylene-di-bromide, etc.). The total bromine in molecular bromine and ionic bromide is used to determine satisfaction of the elemental bromine-to-total cobalt and manganese milligram atom ratios described hereinbelow. The bromine ion released from the organic bromides at the oxidation operating conditions can be readily determined by known analytical means. Tetrabromoethane, for example, at operating temperatures of 170° C. to 225° C. has been found to yield about 3 effective gram atoms of bromine per gram mole.

The weight ratio of cobalt (calculated as elemental cobalt) in the cobalt component of the catalyst-to-aromatic feed compound in the liquid phase oxidation is in the range of from about 0.5 to about 35, preferably from about 2 to about 25, mmoles per mole. The weight ratio of manganese (calculated as elemental manganese) in the manganese component of the catalyst-to-aromatic feed compound is in the range of from about 0.5 to about 35, preferably from about 4 to about 25, mmoles per mole. The weight ratio of bromine (calculated as elemental bromine) in the bromine component of the catalyst-to-aromatic feed compound is in the range of from about 0.5 to about 200, preferably from about 50 to about 150, mmoles per mole.

In operation, the minimum pressure at which the oxidation reactor is maintained is that pressure which will maintain a substantial liquid phase of the aromatic feedstock compound and at least 70 percent of the solvent. The aforesaid aromatic feedstock compound and solvent not in the liquid phase because of vaporization are vented from the oxidation reactor with the excess oxygen as a vapor-gas mixture, condensed, and then returned to the oxidation reactor. When the solvent is a mixture of acetic acid and up to 70 weight percent of water, suitable reaction gauge pressures in the oxidation reactor are in the range of from about 0 $kg/cm^2$ to about 35 $kg/cm^2$, and typically are in the range of from about 10 $kg/cm^2$ to about 30 $kg/cm^2$.

An essential feature of the method of this invention is the addition of water from an external source to the reaction mixture, after initiation of the oxidation of the aforesaid substituted aromatic feed compound. Water from an external source is added to the reaction mixture in an amount of from about 5, preferably from about 10, to about 75, preferably to about 50, and more preferably to about 30, weight percent of the weight of the total solvent of the monocarboxylic acid and water in the reaction mixture during the last two thirds of the stoichiometrically (or theoretically) complete conversion of the aromatic feed compound to the product, preferably during the last half of the aforesaid stoichiometrically complete conversion of the aromatic feed compound to the product. For the purposes hereof, stoichiometrically complete conversion is the theoretically complete conversion of all of the oxidizable substituents of the feed to carboxylic acid groups. Determination of, the first third or first half of the stoichiometrically complete conversion of the feed to the product can be made in a variety of conventional known methods. For example, measurement of the oxygen consumption or analysis of samples of the reaction mixture withdrawn from the reactor could be used for this determination. Preferably the rate of addition of the water from an external source is from about 0.002, preferably from about 0.02, to about 1.0, preferably to about 0.5, gram of water per minute per gram of monocarboxylic acid solvent. The addition of water from an external source can commence either at or subsequent to the initiation of the oxidation of the method of this invention.

In addition to the water added from an external source, water can also be present in the reaction mixture at the time of initiation of the oxidation reaction in an amount of up to about 50, preferably up to about 20, and more preferably up to about 5, percent by weight of the weight of the aliphatic monocarboxylic acid solvent. Moreover, the oxidation reaction itself serves as an internal source of water, which is generated along with the aromatic polycarboxylic acid. The total amount of water that can be present in the reaction mixture from all sources combined—that is, as initially present at the initiation of the oxidation reaction, as introduced as a reaction by-product from the internal source of the oxidation reaction, and as introduced from the external source—is in the range of from about 5, preferably from about 10, to about 92, preferably to about 65, and more preferably to about 40, weight percent of the total solvent of the aliphatic monocarboxylic acid and water.

Another essential feature of the method of this invention is that the temperature of the reaction mixture is increased after initiation of the oxidation reaction from a temperature in the range of from about 93° C., preferably from about 121° C., to about 199° C., preferably to about 188° C. during the aforesaid first third of the stoichiometrically complete conversion, by at least 14° C., preferably at least 28° C., to a temperature in the range of from about 176° C., preferably from about 204° C., to about 249° C., preferably to about 232° C., during the aforesaid last two thirds of the stoichiometrically complete conversion, preferably during the aforesaid last half of the stoichiometrically complete conversion. Preferably the rate of temperature increase is from about 0.2° C./min., preferably from about 1.7° C./min., to about 11° C./min., preferably to about 6° C./min. The increase of the temperature can commence either at or subsequent to the initiation of the oxidation in the method of this invention. In order to maintain liquid-phase conditions, the reaction pressure must also be increased from an initial pressure of from about 10.0 to about 20.0 pounds per square inch gauge at the initiation of the oxidation reaction to a pressure of from about 300 to about 450 pounds per square inch gauge at the highest temperatures.

It is also preferred in the method of this invention to introduce a portion of at least one of the cobalt, manganese and bromine components of the catalyst subsequent to the initiation of the oxidation reaction, to thereby supplement the amount of such components during the oxidation. For example, of the total amount of the cobalt component employed, from about 5, preferably from about 20, up to about 100, percent by weight is present in the reaction mixture at the initiation of the oxidation; and up to about 95, preferably up to about 80, weight percent of the total amount of cobalt employed is added during the aforesaid last two thirds of the stoichiometrically (or theoretically) complete conversion, preferably during the aforesaid last half of the stoichiometrically complete conversion. Most preferably, 100 weight percent of the cobalt employed is present in the reaction mixture at the initiation of the oxidation reaction. Of the total amount of the manganese component employed, from about 0, preferably from about 10, more preferably from about 30, up to about 100, preferably up to about 50, weight percent is present in the reaction mixture at the initiation of the oxidation reaction; and from about 0, preferably from about 50, up to about 100, preferably up to about 90, more preferably up to about 70, weight percent of the manganese employed is added during the aforesaid last two thirds of the stoichiometrically (or theoretically) complete conversion, preferably during the aforesaid last half of the stoichiometrically complete conversion. Of the total amount of the bromine component employed, from about 5, preferably from about 15, more perferably from about 25, to about 100, preferably to about 50, most preferably to about 40, weight percent is present in the reaction mixture at the initiation of the reaction; and from about 0, preferably from about 50, more preferably from about 60, to about 95, preferably to about 85, more preferably to about 75, weight percent of the total amount of bromine employed is added during the aforesaid last two thirds of the stoichiometrically (or theoretically) complete conversion, preferably during the aforesaid last half of the stoichiometrically complete conversion. Most preferably, the cobalt, manganese and bromine components added subsequent to initiation of the oxidation reaction are added as dissolved in the water being added from an external source and at the same rate as is the water from an external source. Optionally, amounts of one or more additional catalyst components, such as zirconium, or catalyst promoters can also be added after initiation of the oxidation reaction.

The oxidation of the method of this invention can be performed either on a batch, continuous or semi-continuous mode. In the batch mode, the aforesaid substituted aromatic feed compound, solvent and aforesaid initial amounts of the cobalt, manganese and bromine components are initially introduced batchwise into the reactor, and the temperature and pressure of the reactor contents are then raised to the desired levels therefor for the commencement of the oxidation reaction. Air is introduced continuously into the reactor. After commencement of the oxidation reaction—for example, after all of the aromatic feed compound had been completely introduced into the reactor, the temperature of the reactor contents is raised, and water from an external source and optionally additional amounts of one or more of the cobalt, manganese and bromine components are introduced into the reactor, as described hereinabove. In the continuous mode, each of the substituted aromatic feed compound, air, solvent and initial amounts of the catalyst components dissolved in the solvent are continuously introduced through a first inlet or set of inlets into a first oxidation reactor where, in an upstream portion thereof, the temperature and pressure are at the desired levels therefor for initiation of the oxidation reaction; and a product stream comprising aromatic polycarboylic acid product and catalyst components dissolved in the solvent is withdrawn from the reactor. Water from an external source and optionally additional amounts of one or more of the cobalt, manganese and bromine components are introduced into the reactor at points downstream of the aforesaid first inlet(s) in the first reactor, or into a second oxidation reactor containing the effluent from the aforesaid first oxidation reactor. In the semi-continuous mode, the solvent and initial amounts of the cobalt, manganese, and bromine components are initially introduced batchwise into the reactor, and then the substituted aromatic feed compound and air are introduced continuously into the reactor. After commencement of the oxidation reaction, the temperature of the reactor contents is raised, and water from an external source and optionally additional amounts of one or more of the cobalt, manganese and bromine components are introduced into the reactor, as described hereinabove. Preferably, the semi-continuous mode is employed for the oxidation of the method of this invention.

Thereafter, the product stream in the continuous mode or the reactor contents in the batch or semi-continuous mode are cooled to a temperature in the range of from about 10° C. to about 120° C., preferably from about 20° C. to about 32° C., at which temperature the resulting crude, solid acid product is separated by filtration or centrifugation from the product mixture. The use of lower temperatures results in the recovery of a significantly less pure product and the use of higher temperatures results in the recovery of significantly less product.

The separated crude aromatic polycarboxylic acid is substantially purified by recrystallizing it at least once from its solution in water, acetic acid or nitric acid as the solvent, using a weight ratio of solvent-to-acid of from about 1:1 to about 10:1, preferably from about 3:1 to about 4:1. At lower solvent-to-acid weight ratios, impurities in the crude acid are insufficiently removed; and at higher solvent-to-acid weight ratios, the recovery of purified acid product is substantially reduced. Preferably water is the recrystallization solvent. The acid is crystallized at a temperature of 20°-130° C.

Although recrystallization alone dramatically improves the purity of the aromatic polycarboxylic acid product, the observed color of the acid product can be further improved and a white product produced if the crude acid product is subjected to treatment with a carbon adsorbent during the aforesaid recrystallization. In such case, while the acid product is dissolved in the recrystallization solvent, the solution is contacted with a carbon adsorbent, typically at a level of, for example, about 3-6 weight percent of the dissolved acid. The solid adsorbent is separated from the solution before the purified acid product is recrystallized from it. Because of the acidic nature of the recrystallization solution, carbon adsorbents having a low content of acid-soluble impurities, such as metal impurities, are useful for this application. Suitable such useful carbon adsorbents include Westvaco's Nuchar SN or SA-20 and American Norit's Darco S51. The purified aromatic polycarboxylic acid product resulting from this carbon treatment has a substantially improved (whiter) color as indicated by its optical density or visual appearance.

Optionally further removal of metal impurities can be effected by treatment of the crude aromatic polycarboxylic acid product with an ion exchange resin during the aforesaid recrystallization. While the acid product is dissolved in the recrystallization solvent, the solution is contacted with a strong acid ion exchange resin containing, for example, sulfonic acid groups in the hydrogen form. Suitable such resins include Rohm & Haas' Amberlite IR-120 and Dow Chemical's Dowex-50W-X8. This ion exchange treatment can be performed simultaneously with the carbon adsorbent treatment or after the carbon adsorbent has been separated from such solution.

Optionally, after the crude acid product is separated from the product mixture and before the aforesaid recrystallization, a wash or reslurry of the crude product with, or in, a liquid which is a relatively poor solvent for the acid product, such as acetic acid, water or mixtures thereof, at a temperature in the range of 0°-50° C. affords a further reduction in impurities.

The present invention will be more clearly understood from the following specific examples.

EXAMPLES 1-26

Except as indicated hereinbelow, in each of Examples 1-26, 0.047 mole of pyromellitic acid was dissolved in 100.0 milliliters of an acetic acid/water mixture at 95° C. 0.0024 mole of cobalt(II) acetate tetrahydrate, 0.0024 mole of manganese(II) acetate tetrahydrate, 0.0048 mole of the bromide source, and 0.000185 mole of zirconium(IV) oxide acetate was then added to the dissolved pyromellitic acid with continuous stirring at 95° C. After 15 minutes, the mixture was filtered through a hot funnel, and the resulting separated solids were air dried and weighed. 50 ml of water was added to the filtrate and the filtrate analyzed for the elements of interest. No pyromellitic acid was employed in Example 2. In each example, the weight percent of each of the cobalt, manganese and bromine components that was dissolved in the acetic acid/water mixture was determined by dividing the number of moles of metal present in solution after the experiment by the number of moles added initially, expressed on a percentage basis.

For each example, the composition of the acetic acid/water mixture, the source of the bromine component, the weight percent of catalyst component dissolved, and the weight of the precipitate formed are presented in Table 1.

TABLE 1

| Example | Concentration of Water in HOAc, Wt. % | Bromine Source | Wt. % of Catalyst Component Dissolved | | | Amount of Solids, gms |
|---|---|---|---|---|---|---|
| | | | Co | Mn | Br | |
| 1 | 0 | HBr | 45 | 23 | 81 | 10.84 |
| 2 | 20 | HBr | 98 | 96 | 93 | none |
| 3 | 20 | HBr | 81 | 57 | 89 | 0.875 |
| 4 | 20 | HBr | 81 | 56 | 95 | 0.64 |
| 5 | 20 | HBr | 87 | 30 | 89 | 0.87 |
| 6 | 25 | HBr | 65 | 76 | 96 | 0.68 |
| 7 | 25 | HBr | 59 | 88 | 90 | 0.63 |
| 8 | 30 | HBr | 83 | 91 | 95 | 0.41 |
| 9 | 30 | HBr | 66 | 87 | 95 | 0.61 |
| 10 | 35 | HBr | 96 | 95 | 97 | 0.11 |
| 11 | 40 | HBr | 100 | 96 | 98 | 0.05 |
| 12 | 40 | HBr | 141 | 102 | 87 | 0.16 |
| 13 | 40 | HBr | 102 | 95 | 94 | 0.12 |
| 14 | 50 | HBr | 102 | 96 | 97 | 0.06 |
| 15 | 60 | HBr | 99 | 92 | 92 | 0.12 |
| 16 | 60 | HBr | 93 | 92 | 97 | 0.08 |
| 17 | 70 | HBr | 94 | 94 | 97 | 0.04 |
| 18 | 80 | HBr | 94 | 91 | 97 | 0.03 |
| 19 | 90 | HBr | 104 | 96 | 94 | 0.04 |
| 20 | 100 | HBr | 93 | 89 | 89 | 0.02 |
| 21 | 20 | NaBr | 38 | 7.2 | 81 | 1.33 |
| 22 | 20 | NaBr | 32 | 32 | 87 | 1.20 |
| 23 | 30 | NaBr | 45 | 66 | 92 | 0.92 |
| 24 | 40 | NaBr | 49 | 82 | 94 | 0.72 |
| 25 | 60 | NaBr | 100 | 97 | 91 | 0.09 |
| 26 | 100 | NaBr | 100 | 93 | 91 | 0.03 |

EXAMPLES 27-40

For each of Examples 27-40, the procedure of Examples 1-26 was repeated, except that hemimellitic acid was used instead of pyromellitic acid. For each example, the composition of the acetic acid/water mixture, the source of the bromine component, the weight percent of catalyst component dissolved, and the weight of the precipitate formed are presented in Table 2.

TABLE 2

| Example | Concentration of Water in HOAc, Wt. % | Bromine Source | Wt. % of Catalyst Component Dissolved | | | Amount of Solids, gms |
|---|---|---|---|---|---|---|
| | | | Co | Mn | Br | |
| 27 | 0 | HBr | 51 | 11 | 90 | 1.09 |
| 28 | 5 | HBr | 64 | 34 | 94 | 0.79 |
| 29 | 10 | HBr | 52 | 59 | 92 | 1.11 |
| 30 | 15 | HBr | 35 | 66 | 92 | 1.44 |
| 31 | 20 | HBr | 50 | 70 | 91 | 1.07 |
| 32 | 30 | HBr | 79 | 89 | 92 | 0.847 |
| 33 | 40 | HBr | 108 | 107 | 96 | 0.14 |
| 34 | 50 | HBr | 101 | 98 | 96 | 0.012 |
| 35 | 0 | NaBr | 68 | 15 | 92 | 0.866 |
| 36 | 5 | NaBr | 71 | 31 | 93 | 0.696 |
| 37 | 10 | NaBr | 51 | 51 | 92 | 1.11 |
| 38 | 15 | NaBr | 33 | 61 | 96 | 1.49 |
| 39 | 20 | NaBr | 54 | 66 | 91 | 1.13 |

TABLE 2-continued

| Example | Concentration of Water in HOAc, Wt. % | Bromine Source | Wt. % of Catalyst Component Dissolved | | | Amount of Solids, gms |
|---|---|---|---|---|---|---|
| | | | Co | Mn | Br | |
| 40 | 30 | NaBr | 60 | 74 | 91 | 1.04 |

EXAMPLES 41–54

For each of Examples 41–54, the procedure of Examples 1–26 was repeated, except that trimellitic acid was used instead of pyromellitic acid. For each example, the composition of the acetic acid/water mixture, the source of the bromine component, the weight percent of catalyst component dissolved, and the weight of the precipitate formed are presented in Table 3.

TABLE 3

| Example | Concentration of Water in HOAc, Wt. % | Bromine Source | Wt. % of Catalyst Component Dissolved | | | Amount of Solids, gms |
|---|---|---|---|---|---|---|
| | | | Co | Mn | Br | |
| 41 | 0 | HBr | 61 | 50 | 92 | 5.63 |
| 42 | 5 | HBr | 63 | 53 | 94 | 2.48 |
| 43 | 10 | HBr | 89 | 89 | 97 | 0.183 |
| 44 | 15 | HBr | 87 | 92 | 99 | 0.030 |
| 45 | 20 | HBr | 99 | 99 | 98 | 0.024 |
| 46 | 30 | HBr | 99 | 94 | 96 | 0.036 |
| 47 | 40 | HBr | 98 | 94 | 93 | 0.042 |
| 48 | 50 | HBr | 96 | 96 | 91 | 0.050 |
| 49 | 0 | NaBr | 20 | 5.1 | 84 | 5.90 |
| 50 | 5 | NaBr | 24 | 13 | 81 | 2.62 |
| 51 | 10 | NaBr | 76 | 30 | 93 | 0.981 |
| 52 | 15 | NaBr | 90 | 54 | 92 | 0.595 |
| 53 | 20 | NaBr | 99 | 98 | 89 | 0.079 |
| 54 | 30 | NaBr | 99 | 94 | 92 | 0.074 |

Tables 1, 2 and 3 illustrate that each of pyromellitic acid (1,2,4,5-tetracarboxybenzene, the oxidation product of durene), hemimellitic acid (1,2,3-tricarboxybenzene, the oxidation product of 1,2,3-trimethylbenzene), and trimellitic acid (1,2,4-tricarboxylbenzene, the oxidation product of pseudocumene) respectively, precipitates colbalt(II) acetate and manganese(II) acetate from a typical solution used in homogeneous oxidation. A typical water concentration inside a reactor during a homogeneous oxidation is about 20%. Example 21 on Table 1 illustrates that at this water concentration, using sodium bromide as the bromide source, 62% of the cobalt had precipitated and 93% of the manganese had precipitated. Similar results are illustrated for hemimellitic acid (the product of 1,2,3-trimethylbenzene) in Table 2 and for trimellitic acid (the product of pseudocumene) in Table 3. Importantly, Tables 1–3 also illustrate that the catalyst precipitation ceases after a certain amount of water has been added to the acetic acid. For pyromellitic acid and hemimellitic acid this limit is about 40% water in the acetic acid, while for trimellitic acid, the limit is about 20% (using hydrogen bromide as the bromide source—sodium bromide has higher limits).

EXAMPLES 55–59

Homogeneous oxidations of pseudocumene were performed on a batch basis in a glass reactor in which air was passed through the acetic acid solvent via a glass frit. 100.0 milliliters of acetic acid, 10.0 milliliters of pseudocumene, 0.002 mole of cobalt(II) acetate tetrahydrate, 0.002 mole of manganese(II) acetate tetrahydrate, 0.004 mole of sodium bromide were initially placed in the reactor. The water and an aromatic acid (described below) were added incrementally during the oxidation. The temperature of the reaction was 95° C., the pressure ambient atmospheric, and the flow rate of air 52 milliliter per minute. The rate of oxidation was determined by measuring the oxygen content of the vent gas and knowing the flow rate of air through the reactor.

A plot of the oxidation rate versus the mole ratio of the aromatic acid added-to-the metal components of the catalyst is presented in FIG. 1. FIG. 1 illustrates that the precipitation of the catalyst metals retards the rate of oxidation and, if in high enough concentrations, completely inhibits the reaction. The homogeneous oxidation was purposely made to occur very slowly so that the rate of oxidation would be constant for a number of hours. While the homogeneous oxidation was in progress, increments of selected acids were added. Acids such as benzoic and phthalic had little effect on the rate of oxidation and no precipitation occurred in the glass reactor. However, addition of trimellitic, hemimellitic, and pyromellitic acids caused precipitation of the metals in the reactor and, at first, severely inhibited the reaction, and when in sufficient concentration, caused the oxidation to cease.

EXAMPLES 60–69

Each of Examples 60–69 involves the oxidation of the durene on a batch basis and was performed in a two liter autoclave equipped with a stirrer, air line, cooling coil, and additional lines for introduction of material during the oxidation. The temperature of the reactor was controlled by insulated electrical heaters which surrounded the autoclave, and the cooling coil in the reactor. A controlled rate of fluid was passed through the cooling coil during the oxidation. The vented gases from the reactor were passed through a series of condensers, cooled by dry-ice, and then through instruments which recorded the gaseous flow rate and the concentration of oxygen and carbon dioxide in the gas stream. Typically, the reagents were added to the autoclave, and the reactor was purged with a slow addition of nitrogen gas. The temperature of the reactor was brought up to the initiation temperature and then the reaction started by stopping the nitrogen gas flow and starting a flow of air through the reactor. The pressure of the reactor was controlled by a research control valve. Reagents were added into the autoclave during the reaction by a suitable pump. The rate of oxidation was determined by measuring the oxygen content of the vent gas and knowing the flow rate of air through the reactor and was employed as a measure of the extent of conversion of durene to pyromellitic acids. The reaction was terminated by the replacement of the flow of air into the reactor with a flow of nitrogen gas into the reactor. Catalyst metal components were introduced in the form of their acetate tetrahydrates, and the bromine component was added as HBr.

Table 4 gives a typical time-temperature-pressure-catalyst addition profile during a batch oxidation of durene. A pump was used to slowly add a catalyst mixture dissolved in a solvent. At 50 minutes, when the durene was approximately 80% oxidized and significant amounts of pyromellitic acids had begun to form in the reactor, the rate of addition of water was greatly increased so that the water concentration was rapidly increased inside the reactor. Catalyst metals were dissolved in the water pumped into the reactor so that the deactivating effect of the water was compensated by additional catalyst.

Examples 60-69 illustrate the effect of increasing the pump rate into the reactor after 50 minutes into the reaction. This increases the water content at the end of the oxidation, as shown in Table 5, and results in the yield increasing from 66 to 80 molar percent pyromellitic acid. Table 5 also illustrates that the level of reaction intermediates, the sum of the dicarboxyphthalide and tricarboxyltoluene, drop from 19.6 to 14.4 to 9.94 to 1.6, indicating that the reaction has gone increasingly farther to completion. This can also be seen by the increase in acid number of the solids obtained after the reactor effluent is cooled. In Examples 60-64 the increase is 834, 845, 860 to 878 (883 is the theoretical value for 100% pure pyromellitic acid). The beneficial effect of water can also be seen by comparing Example 63 and 69. In Example 69, the water in the pump was replaced by acetic acid. This resulted in a large decrease in the amount of water added to the reactor, and the yield decreased from 80 to 64 percent with a concomitant decrease in the acid number from 878 to 853. Examples 62 and 68 are similar. The other examples on Table 6 employed varying amounts of catalyst in the pump solution and also afforded high yields to pyromellitic acid and high acid numbers.

TABLE 4

| Time, Min. | Flow Rate of Air, Cubic ft/min | Pressure lbs/in² | Temp., °C. | Total Amount Pumped Into The Reactor | | |
|---|---|---|---|---|---|---|
| | | | | Water, g | Manganese, mmole | Bromide, mmole |
| 0 | 0.78 | 150 | 138 | 0 | 0 | 0 |
| 5 | 0.78 | 150 | 139 | 3 | 0.064 | 1.0 |
| 10 | 0.78 | 150 | 144 | 6 | 0.14 | 2.0 |
| 15 | 0.78 | 150 | 149 | 9 | 0.21 | 3.0 |
| 20 | 0.78 | 200 | 152 | 12 | 0.28 | 4.1 |
| 25 | 0.78 | 200 | 156 | 15 | 0.35 | 5.1 |
| 30 | 0.78 | 225 | 158 | 18 | 0.42 | 6.1 |
| 35 | 0.78 | 250 | 163 | 21 | 0.49 | 7.1 |
| 40 | 0.78 | 275 | 164 | 24 | 0.56 | 8.1 |
| 45 | 0.78 | 300 | 177 | 27 | 0.62 | 9.1 |
| 50 | 0.78 | 350 | 204 | 30 | 0.69 | 10.1 |
| 55 | 0.48 | 400 | 220 | 70 | 1.62 | 23.8 |
| 60 | 0.48 | 450 | 226 | 110 | 2.54 | 37.3 |
| 65 | 0.48 | 450 | 228 | 150 | 3.47 | 50.9 |
| 70 | 0.48 | 450 | 226 | 190 | 4.39 | 64.4 |
| 75 | 0.48 | 450 | 226 | 230 | 5.32 | 78.1 |
| 80 | 0.48 | 450 | 227 | 270 | 6.24 | 91.6 |
| 85 | 0.48 | 450 | 227 | 310 | 7.17 | 105 |
| 90 | 0.48 | 450 | 227 | 360 | 8.32 | 122 |
| 95 | 0.48 | 450 | 225 | 400 | 9.25 | 136 |
| 100 | 0.48 | 450 | 224 | 400 | 9.25 | 136 |
| 105 | 0.48 | 450 | 224 | 400 | 9.25 | 136 |
| 110 | 0.48 | 450 | 224 | 400 | 9.25 | 136 |

TABLE 5

| | Example | | | | |
|---|---|---|---|---|---|
| | 60 | 61 | 62 | 63 | 64 |
| Initial Charge in Reactor | | | | | |
| Durene, g | 184.24 | 184.24 | 184.24 | 184.24 | 184.24 |
| Acetic acid, g | 400 | 400 | 400 | 400 | 400 |
| Water, g | 21 | 21 | 21 | 21 | 21 |
| Cobalt, mmole | 13.1 | 13.1 | 13.1 | 13.1 | 13.1 |
| Manganese, mmole | 4.1 | 4.1 | 4.1 | 4.1 | 4.1 |
| HBr, mmole | 3.1 | 3.1 | 3.1 | 3.1 | 3.1 |
| Zirconium, mmole | 0.198 | 0.198 | 0.198 | 0.198 | 0.198 |
| Added During Reaction Via Pump | | | | | |
| Acetic acid, g | 68.8 | 0 | 0 | 0 | 0 |
| Water, g | 12.5 | 97.1 | 166.1 | 365 | 381 |
| Cobalt, mmole | 0 | 0 | 0 | 0 | 30.9 |
| Manganese, mmole | 2 | 2.5 | 4.2 | 9.3 | 9.6 |
| HBr, mmole | 28.5 | 35.2 | 60.5 | 132.9 | 138.2 |
| Zirconium, mmole | 0.596 | 0.745 | 1.286 | 2.833 | 2.795 |
| Molar Yield, % | | | | | |
| Pyromellitic Acid | 66 | 66 | 71 | 80 | 80 |
| Trimellitic Acid | 1.66 | 0.74 | 1.48 | 1.41 | 1.46 |
| 1,2-dicarboxyphthalide | 8.48 | 6.16 | 4.03 | 1.12 | 1.29 |
| 2,4,5-tricarboxy toluene | 11.14 | 8.28 | 5.91 | 0.52 | 0.58 |
| Acid No. | 834 | 845 | 860 | 878 | 871 |
| % Burning of hydrocarbon | 4 | 4.6 | 4.9 | 7.4 | 7.1 |

TABLE 6

| | Example | | | | |
|---|---|---|---|---|---|
| | 65 | 66 | 67 | 68 | 69 |
| Initial Charge in Reactor | | | | | |
| Durene, g | 184.24 | 184.24 | 184.24 | 184.24 | 184.24 |
| Acetic acid, g | 400 | 400 | 400 | 399 | 400 |
| Water, g | 21 | 21 | 21 | 21 | 21 |
| Cobalt, mmole | 13.1 | 13.1 | 13.1 | 13.1 | 13.1 |
| Manganese, mmole | 4.1 | 4.1 | 4.1 | 4.1 | 4.1 |
| HBr, mmole | 3.1 | 3.1 | 3.3 | 3.1 | 3.1 |
| Zirconium, mmole | 0.198 | 0.198 | 0.198 | 0 | 0.198 |
| Added During Reaction Via Pump | | | | | |
| Acetic acid, g | 0 | 0 | 0 | 180 | 240 |
| Water, g | 369 | 341 | 443 | 0 | 0 |
| Cobalt, mmole | 59.8 | 0 | 0 | 0 | 0 |
| Manganese, mmole | 18.7 | 8.6 | 11.2 | 4.3 | 5.8 |
| HBr, mmole | 267.6 | 123.4 | 160.8 | 62.4 | 83.1 |
| Zirconium, mmole | 5.74 | 1.325 | 3.448 | 1.334 | 1.782 |
| Molar Yield, % | | | | | |
| Pyromellitic Acid | 83 | 82 | 83 | 71 | 64 |
| Trimellitic Acid | 1.64 | 1.09 | 2.07 | 1.99 | 2.51 |
| 1,2-dicarboxyphthalide | 1.03 | 1.05 | 1.08 | 5.64 | 3.6 |
| 2,4,5-tricarboxy toluene | 0.32 | 0.29 | 0.4 | 12.69 | 8.34 |
| Acid No. | 870 | 870 | 874 | 845 | 853 |
| % Burning of hydrocarbon | 7.4 | 6.8 | 6.8 | 3.9 | 5.6 |

EXAMPLES 70-75

Each of Examples 70-75 involves the oxidation of durene on a semi-continuous basis. In these examples, an acetic acid solvent and initial amounts of the cobalt, manganese (added in the form of their acetate tetrahydrates), and bromine (added as HBr) components of the catalyst were introduced batchwise into a two-liter reactor equipped essentially the same as the reactor employed in Examples 60-69. The temperature and pressure of the reactor contents were raised to the desired levels therefor for commencement of the oxidation, and then durene at a rate of 3.2 grams per minute and air were introduced continuously into the reactor. Immediately after all of the durene had been introduced (which required 55 minutes in each of Examples 70–75), the temperature of the reactor contents was raised and water from an external source containing additional amounts of the manganese and bromine catalyst components and initial amounts of the zirconium component of the catalyst system were introduced into the reactor.

The conditions employed in and results from Examples 70–75 are presented in Table VII. As employed in Table VII, the term "first" refers to the reaction temperature and volume ratio of solvent-to-feed as introduced at the time when the addition of durene is complete and immediately before the temperature of the reactor contents was raised at about 1.9° C./min. Throughout this first period, the reaction temperature was essentially constant. The term "second" refers to the average highest temperature of the reactor contents and the weight ratio of solvent-to-feed when all the water and feed have been introduced. Comparison of the results from Example 70 with the results from Examples 71, 72 and 73 illustrates the affect of changes in the amount of water added, final reaction temperature and total reaction time, respectively, and comparison of the results of Examples 74 and 75 illustrates the effect of the rate of addition of water. As employed herein, "PMA" means pyromellitic acid, "TMLA" means trimellitic acid, "1,2-DCP" means 1,2-dicarboxy-4,5-phthalide; and "2,4,5-TCT" means 2,4,5-tricarboxytoluene.

TABLE 7

| | Example | | | | | |
|---|---|---|---|---|---|---|
| | 70 | 71 | 72 | 73 | 74 | 75 |
| Initial Change in Reactor | | | | | | |
| $C_2H_3O_2H$ (gm) | 800 | 800 | 800 | 800 | 800 | 800 |
| $H_2O$ (gm) | 40 | 40 | 40 | 40 | 40 | 40 |
| Co mmoles | 4.8 | 4.8 | 4.8 | 4.8 | 4.8 | 4.8 |
| Mn mmoles | 2.0 | 2.0 | 2.0 | 2.0 | 2.0 | 2.0 |
| Br mmoles | 1.2 | 1.2 | 1.2 | 1.2 | 1.2 | 1.2 |
| Added During Reaction Via Pump | | | | | | |
| Durene[1] (gm) | 177 | 177 | 177 | 177 | 177 | 177 |
| Aq. Solu. | | | | | | |
| Volume (ml) | 420 | 420 | 420 | 420 | 350 | 350 |
| Rate (ml/min) | 17.6 | 17.6 | 17.6 | 17.6 | 17.6 | 10.0 |
| Components | | | | | | |
| Mn (mmoles) | 21.8 | 21.8 | 21.8 | 21.8 | 18.1 | 18.1 |
| Br (mmoles) | 99.8 | 99.8 | 99.8 | 99.8 | 83.1 | 18.1 |
| Zr (mmoles) | 2.7 | 2.7 | 2.7 | 2.7 | 2.2 | 2.2 |
| $H_2O^2$ (wt. %) | 34 | 17 | 34 | 34 | 30 | 30 |
| Temp. (°C.) | | | | | | |
| First | 171 | 171 | 177 | 177 | 171 | 177 |
| Second | 227 | 227 | 218 | 227 | 227 | 227 |
| Solvent:Feed (wt.) | | | | | | |
| First | 4.7 | 4.7 | 4.7 | 4.7 | 4.7 | 4.7 |
| Second | 7.0 | 7.0 | 7.0 | 7.0 | 6.7 | 6.7 |
| Total $H_2O$ | | | | | | |
| Conc.[3] (wt. %) | 40 | 26 | 40 | 40 | 37 | 37 |
| Rx time (min) | 145 | 135 | 135 | 120 | 135 | 135 |
| Yields[4] (mole %) | | | | | | |
| PMA | 84.0 | 65.8 | 78.0 | 72.0 | 80.2 | 77.0 |
| TMLA | 2.8 | 3.5 | 2.8 | 2.8 | 3.0 | 2.9 |
| 1,2-DCP | 2.5 | 5.1 | 3.9 | 4.3 | 4.0 | 3.0 |

TABLE 7-continued

| | Example | | | | | |
|---|---|---|---|---|---|---|
| | 70 | 71 | 72 | 73 | 74 | 75 |
| 2,4,5-TCT | 1.0 | 4.5 | 1.4 | 2.3 | 2.6 | 1.4 |

Footnotes:
[1] 95 wt. % pure durene.
[2] water added from an external source, based on the total weight of acetic acid and water
[3] the final concentration of water from all sources, based on the total weight of acetic acid and water.
[4] based on durene charged.

EXAMPLES 76–78

In each of Examples 76–78, 100 parts of crude pyromellitic acid prepared by oxidation of durene in accordance with the method of this invention was washed with 150 parts of water at 25° C. Thereafter, in each of Examples 77 and 78 the washed crude pyromellitic acid was recrystallized once or twice, respectively, from 400 parts of water at 24°–82° C. The optical densities of, and concentrations of organic and inorganic impurities in, each of the crude pyromellitic acid employed in Examples 76–78, the washed pyromellitic acid and the singly and doubly recrystallized pyromellitic acid, and the percent of pyromellitic acid recovered in each recrystallization are presented in Table 8.

TABLE 8

| | Crude PMA | Example | | |
|---|---|---|---|---|
| | | 76 | 77 | 78 |
| No. of recrystallizations | | 0 | 1 | 2 |
| PMA recovery (wt. %)[1] | | 93.0 | 90.8 | 93.1 |
| PMA optical density[2] | | 1.39 | 0.68 | 0.40 |
| Concentration of impurities in PMA (ppm wt.)[3] | | | | |
| Organic | | | | |
| TMLA | 8910 | 6802 | 1796 | 623 |
| 1,2-DCP | 11363 | 6526 | 1049 | 211 |
| 2,4,5-TCT | 10511 | 7383 | 2888 | 1282 |
| Inorganic[4] | | | | |
| Co | 169 | 68 | 7 | <4 |
| Mn | 1230 | 1020 | 12 | 5 |
| Br | 1290 | 162 | 47 | 21 |
| Zr | 690 | 780 | 57 | 18 |
| Fe | 5 | <4 | 69 | 12 |

Footnotes:
[1] based on the initial weight of PMA
[2] measured at 300 nanometers
[3] based on the weight of solid PMA recovered
[4] calculated as the elemental metals

EXAMPLES 79–80

In each of Examples 79–80, 100 parts of crude pyromellitic acid prepared by oxidation of durene in accordance with the method of this invention was recrystallized once from 40 parts of water at 25° C. In addition, in Example 80, while the pyromellitic acid was dissolved during the recrystallization process, 3 parts of Darco S-51 was mixed with the solution, and the mixture was stirred at 100° C. for 30 minutes, after which time the carbon was separated from the solution by filtration; thereafter the solution was cooled to 30° C. to recrystallize the pyromellitic acid. The optical densities of, and concentrations of organic and inorganic impurities in, each of the crude pyromellitic acid employed in Examples 79 and 80, the recrystallized pyromellitic acid and the recrystallized and carbon-treated pyromellitic acid, and the percent of pyromellitic acid recovered in each recrystallization are presented in Table 9.

TABLE 9

| | Crude PMA | Example 79 | Example 80 |
|---|---|---|---|
| Adsorbent | | none | carbon |
| PMA recovery (wt. %)[1] | | 85.0 | 85.0 |
| Recovered PMA color | yellow | yellow | white |
| Concentration of impurities in PMA (ppm wt.)[2] | | | |
| Organic | | | |
| TMLA | 6600 | 1320 | 1590 |
| 1,2-DCP | 5500 | 350 | 380 |
| 2,4,5-TCT | 2400 | 830 | 960 |
| Inorganic[3] | | | |
| Co | 850 | 46 | 22 |
| Mn | 3750 | 200 | 101 |
| Br | 6200 | 440 | 40 |
| Zr | 620 | 530 | 45 |

Footnotes:
[1] based on the initial weight of PMA
[2] based on the weight of solid PMA recovered
[3] calculated as the elemental metals

EXAMPLES 81-86

In each of Examples 81-86, 100 parts of crude pyromellitic acid prepared by oxidation of durene in accordance with the method of this invention was recrystallized once or twice from 400 parts of water at 25° C. Furthermore, in each example, while the pyromellitic acid was dissolved during the recrystallization process, 3 parts of a carbon adsorbent were mixed with the solution, and the mixture was stirred at 100° C. for 30 minutes, after which time the carbon was separated from the solution by filtration; thereafter the solution was cooled to 30° C. to recrystallize the pyromellitic acid. The optical densities of, and concentrations of organic and inorganic impurities in, each of the crude pyromellitic acid employed in Examples 81 and 86, the recrystallized and carbon-treated pyromellitic acid, and the percent of pyromellitic acid recovered in each recrystallization are presented in Table 10.

EXAMPLE 87

25 grams of crude pyromellitic acid was dissolved in 100 grams water at 100° C., and 0.5 grams of Nuchar S-N carbon was added. The solution was kept at 100° C. for 60 minutes and filtered hot through a bed of diatomaceous filter aid. The filter was washed with 10 grams of boiling water. The product was cooled to 20° C., allowing the pyromellitic acid to crystallize. The resulting slurry was filtered, and the cake was washed with 12.5 grams water. The cake was then dried for 16 hours at 90° C. and 20″ Hg vacuum. 21.7 grams of dry solids were recovered. The metals analyses of the crude and purified materials are given in Table 11.

EXAMPLE 88

25 grams of crude pyromellitic acid was dissolved in 100 grams water at 100° C., and 0.5 grams of Nuchar S-N carbon was added. The solution was kept at 100° C. for 30 minutes; 15 grams Amberlite IR-120 (hydrogen form) was added; the mixture was kept at 100° C. for an additional 30 minutes and filtered hot through filter aid. The product was then worked up in the same manner as in Example 90. 18.9 grams of dry cake was recovered. The metals analyses are given in Table 11.

A comparison with the results of Example 87 shows that the cobalt and manganese concentrations in the product are much lower than when no ion exchange treatment was used, but that metals which may be derived from the carbon or the filter aid, or both, such as aluminum, calcium and iron, were not reduced.

EXAMPLE 89

25 grams of crude pyromellitic acid was dissolved in 100 grams water at 100° C., and 0.5 grams of Nuchar S-N carbon was added. The solution was kept at 100° C. for 60 minutes and filtered hot through filter aid. The filter was washed with 10 grams boiling water. 15 grams Amberlite IR-120 ion exchange resin (hydrogen form) was added; the mixture was kept at 100° C. for an additional 30 minutes and filtered hot through a sintered glass filter. The filter was washed with 10 grams of boiling water. The product was cooled to 20° C., allow-

TABLE 10

| | Crude PMA | Example 81 | Example 82 | Example 83 | Example 84 | Example 85 | Example 86 |
|---|---|---|---|---|---|---|---|
| No. of recrystallizations | | 1 | 2 | 1 | 2 | 1 | 2 |
| Type of adsorbent | | DARCO S-51 | DARCO S-51 | DARCO G-60 | DARCO G-60 | NUCHAR SA-20 | NUCHAR SA-20 |
| PMA optical density[1] | 2.040 | 0.66 | 0.44 | 0.71 | 0.49 | 0.58 | 0.37 |
| Concentration of impurities in recovered PMA (ppm wt.)[2] | | | | | | | |
| Organic | | | | | | | |
| TMLA | 10378 | 3839 | 1347 | 3349 | 938 | 3767 | 881 |
| 1,2-DCP | 9406 | 2358 | 494 | 2118 | 341 | 2348 | 293 |
| 2,4,5-TCT | 8343 | 4578 | 2346 | 4420 | 1695 | 4694 | 1523 |
| Inorganic[3] | | | | | | | |
| Co | 640 | 65 | 4 | 63 | <4 | 68 | 5 |
| Mn | 737 | 72 | 4 | 69 | 4 | 74 | 5 |
| Br | 2400 | 235 | 39 | 242 | 41 | 224 | 35 |
| Zr | 423 | 54 | 16 | 41 | 6 | 48 | 5 |
| Fe | 6 | 15 | 19 | 9 | 9 | 10 | 12 |
| Al | 9 | 66 | 48 | 10 | 8 | 13 | 10 |
| Ca | 4 | 49 | 29 | 38 | 32 | 44 | 48 |
| Na | 36 | 28 | 41 | 69 | 13 | 91 | 25 |
| Si | 13 | 68 | 19 | 65 | 19 | 57 | 32 |

Footnotes:
[1] measured at 300 nanometers
[2] based on the weight of solid PMA recovered
[3] calculated as the elemental metals ing the pyromellitic acid to crystallize. The resulting slurry was filtered, and the cake was washed with 12.5 grams water. The cake was then dried for 16 hours at 90° C. and 20" Hg vacuum. 21.4 grams of dry solids was recovered. The metals analyses of the crude and purified materials are given in Table 11. Very low levels of cobalt, manganese, aluminum, calcium and iron were achieved.

EXAMPLE 90

25 grams of crude pyromellitic acid was dissolved in 100 grams water at 100° C., and one gram filter aid (Celite Hyflo Super-Cel) was added. The solution was kept at 100° C. for 120 minutes and filtered hot through a bed of filter aid. The filter was washed with 10 grams of boiling water. The product was cooled to 20° C., allowing the pyromellitic acid to crystallize. The resulting slurry was filtered, and the cake was washed with 12.5 grams water. The cake was then dried for 16 hours at 90° C. and 20" Hg vacuum. 20.8 grams of dry solids was recovered. The metals analyses of the crude and purified materials are given in Table 11.

From the above description, it is apparent that the objects of the present invention have been achieved. While only certain embodiments have been set forth, alternative embodiments and various modifications will be apparent from the above description to those skilled in the art. These alternatives are considered equivalents and within the spirit and scope of the present invention.

TABLE 11

| Metal Concentration (ppm wt) | Crude PMA | Example | | | |
|---|---|---|---|---|---|
| | | 87 | 88 | 89 | 90 |
| Al | NA | 14.2 | 25.4 | 1.7 | 21.4 |
| Ca | 4.4 | 3.0 | 3.0 | 1.2 | 6.0 |
| Co | 910 | 14.0 | 0.12 | 0.92 | 26.4 |
| Cr | 2.0 | 1.1 | 0.7 | 0.2 | 1.2 |
| Cu | 0.5 | 0.2 | 0.2 | 0.2 | 0.3 |
| Fe | 7.5 | 5.8 | 14.8 | 1.6 | 11.0 |
| K | 1.0 | 0.9 | 1.3 | 1.7 | 4.0 |
| Mg | 6.3 | 0.9 | 1.2 | 2.7 | 3.8 |
| Mn | 270 | 4.0 | §0.01 | 0.03 | 7.3 |
| Mo | §0.1 | §0.1 | §0.1 | §0.1 | §0.1 |
| Na | 25.1 | 6.8 | 3.6 | 1.3 | 3.4 |
| Ni | NA | 0.4 | 0.1 | 0.2 | 1.0 |
| P | 3.2 | 2.2 | 2.1 | 2.2 | 4.0 |
| S | 188 | 16 | §1 | §1 | §1 |
| Si | §1.5 | 13.8 | 29.6 | 21.7 | 46.0 |
| Zr | 1540 | 2.5 | 2.6 | 0.9 | 2.9 |

Having described the invention, what is claimed is:

1. A method for producing an aromatic polycarboxylic acid product comprising: oxidizing an aromatic feed compound having a phenyl or naphthyl ring and having at least 3 oxidizable ring substituents, said oxidizable substituents containing from 1 to 3 carbon atoms and comprising alkyl groups or carbonyl groups or a combination of alkyl and carbonyl groups, with at least 2 oxidizable substituents on the phenyl ring or on one ring in the naphthyl ring system ring, with an oxygen-containing gas in the liquid phase at an elevated temperature and pressure in a solvent comprising a $C_2-C_6$ monocarboxylic acid or a mixture thereof with water, and in the presence of an oxidation catalyst comprising cobalt, manganese, and bromine components, with a weight ratio of solvent-to-feed in the range of from about 0.5:1 to about 15:1, wherein the reaction temperature is in the range of from about 93° C. to about 199° C. during the first third of the stoichiometrically complete conversion of the feed to the product and is increased at least about 14° C. to the range of from about 176° C. to about 249° C. in the last two thirds of the aforesaid stoichiometric conversion, and wherein water is added from an external source during the aforesaid last two thirds of the stoichiometrically complete conversion to a level in the range of from about 5 to about 75 weight percent of the total solvent of the monocarboxylic acid and water wherein the total amount of water that is present during the aforesaid last two thirds of the stoichiometrically complete conversion and that is the sum of (1) the amount of water initially present at the initiation of the oxidation reaction, (2) the amount of water produced as by-product of the oxidation reaction, and (3) the amount of water added from an external source after initiation of the oxidation reaction, is in the range of from about 5 to about 92 weight percent of the total solvent of the monocarboxylic acid and sa water.

2. The method of claim 1 wherein at least 2 oxidizable substituents are ortho to each other on the phenyl or naphthyl ring of the aromatic compound feed.

3. The method of claim 1 wherein the aromatic compound feed comprises durene or 2,4,5-trimethylbenzaldehyde.

4. The method of claim 1 wherein water is added from an external source during the aforesaid last two thirds of the stoichiometrically complete conversion to a level in the range of from about 5 to about 50 weight percent of the total solvent of the monocarboxylic acid and water.

5. The method of claim 1 wherein water is added from an external source during the last half of the aforesaid stoichiometrically complete conversion to a level in the range of from about 5 to about 75 weight percent of the total solvent of the monocarboxylic acid and water.

6. The method of claim 1 wherein the reaction temperature is in the range of from about 121° C. to about 188° C. during the aforesaid first third of the stoichiometrically complete conversion and is increased to the range of from about 204° C. to about 232° C.

7. The method of claim 1 wherein the weight ratio of cobalt (calculated as elemental cobalt) in the cobalt component of the catalyst-to-aromatic feed compound in the liquid phase oxidation is in the range of from about 0.5 to about 35 mmoles per mole, the weight ratio of manganese (calculated as elemental manganese) in the manganese component of the catalyst-to-aromatic feed compound is in the range of from about 0.5 to about 35 mmoles per mole, and the weight ratio of bromine (calculated as elemental bromine) in the bromine component of the catalyst-to-aromatic feed compound is in the range of from about 0.5 to 200 mmoles per mole.

8. The method of claim 1 wherein up to 95 weight percent of the total amount of bromine component, calculated as elemental bromine, of the catalyst is introduced in the aforesaid last two thirds of the stoichiometrically complete conversion.

9. The method of claim 8 wherein from about 50 to about 85 weight percent of the total amount of the bromine component, calculated as elemental bromine, of the catalyst is introduced in the aforesaid last two thirds of the stoichiometrically complete conversions.

10. The method of claim 1 wherein up to 100 weight percent of the total amount of the manganese component, calculated as elemental manganese, of the catalyst is introduced in the aforesaid last two thirds of the stoichiometrically complete conversion.

11. The method of claim 10 wherein from about 50 to about 90 weight percent of the total amount of the manganese component, calculated as elemental manganese, of the catalyst is introduced in the aforesaid last two thirds of the stoichiometrically complete conversion.

12. The method of claim 1 wherein up to 95 weight percent of the total amount of the cobalt component, calculated as elemental cobalt, of the catalyst is introduced in the aforesaid last two thirds of the stoichiometrically complete conversion.

13. The method of claim 12 wherein up to about 80 weight percent of the total amount of the cobalt component, calculated as elemental cobalt of the catalyst is introduced in the aforesaid last two thirds of the stoichiometrically complete conversion.

14. The method of claim 1 wherein the weight ratio of monocarboxylic acid solvent-to-aromatic feed compound is in the range of from about 1:1 to about 10:1.

15. The method of claim 1 wherein the oxidation is performed on a semi-continuous basis.

16. The method of claim 1 wherein the resulting aromatic polycarboxylic acid is a crude solid and is separated from the product mixture by filtration or centrifugation at a temperature in the range of from about 10° C. to about 120° C.

17. The method of claim 16 wherein the separated crude acid product is purified by recrystallization at least once from a solvent comprising at least one of water, nitric acid or acetic acid, with a ratio of solvent-to-crude acid product in the range of from about 1:1 to about 10:1 at a temperature in the range of from about 20° C. to about 130° C.

18. The method of claim 17 wherein the separated crude acid product is subjected to treatment with a carbon adsorbent when the acid product is solubilized during the aforesaid at least one recrystallization, and the solid adsorbent is separated from the solution before the purified acid is recrystallized.

19. The method of claim 17 wherein the separated crude acid product is subjected to treatment with a strong acid ion exchange resin when the acid product is solubilized during the aforesaid at least one recrystallization and before the purified, acid is recrystallized.

20. The method of claim 17 wherein the separated crude acid product is washed or reslurried with acetic acid or water at a temperature in the range of from about 0° C. to about 50° C. prior to recrystallization.

* * * * *

UNITED STATES PATENT OFFICE
CERTIFICATE OF CORRECTION

Patent No. 5,041,633                    Dated  August 20, 1991

Inventor(s) Walter Partheimer, Gregory P. Hussmann, Juergen K. Holzhauer & Stephen V. Hoover It is certified that error appears in the above-identified patent and that said Letters Patent is hereby corrected as shown below:

| Col. | Line | |
|------|------|---|
| 4 | 41 | "Determination of," should read --Determination of-- |
| 6 | 64 | "centrifugation-from" should read --centrifugation from-- |
| 16 | 24 | "18.9 grams of dry cake was, recovered" should read --18.9 grams of dry cake was recovered-- |
| 20 | 21 | "purified,acid is" should read --purified acid is-- |

Signed and Sealed this

Twelfth Day of January, 1993

Attest:

DOUGLAS B. COMER

Attesting Officer        Acting Commissioner of Patents and Trademarks